United States Patent [19]

Jarque et al.

[11] 4,111,945

[45] Sep. 5, 1978

[54] PROCESS FOR THE PREPARATION OF 3,4,5-TRIMETHOXY-PHENYL-(1,4-DIMETHYL-1,2,3,6-TETRAHYDRO-2-PYRIDYL)-CARBINOL

[75] Inventors: Ricardo Granados Jarque; Juan Bosch Cartés; Jorge Canals Cabiró, all of Barcelona; Cristóbal Martínez Roldán; Fernando Rabadán Peinado, both of Madrid, all of Spain

[73] Assignee: Laboratories Made, S.A., Madrid, Spain

[21] Appl. No.: 757,175

[22] Filed: Jan. 6, 1977

[30] Foreign Application Priority Data

Jan. 22, 1976 [ES] Spain .................... 444.539

[51] Int. Cl.$^2$ ............................ C07D 211/70
[52] U.S. Cl. ................ 260/297 R; 424/263
[58] Field of Search ............. 260/297 R; 424/263

[56] References Cited

U.S. PATENT DOCUMENTS

| 3,093,650 | 6/1963 | Fry et al. ............ 260/297 R |
| 3,426,030 | 2/1969 | Paragamian .......... 260/297 R |
| 3,839,345 | 10/1974 | Pars ................. 260/297 R |
| 4,000,283 | 12/1976 | Jarque et al. ........ 260/297 R |

OTHER PUBLICATIONS

Granados Jarque et al. II, Chem. Abst., 1976, vol. 84, No. 43870k.
Sankey et al., Chem. Abst., 1976, vol. 84, No. 74112u.
Sankey et al., J. Heterocyclic Chem., 1972, vol. 9, pp. 1049–1055.

*Primary Examiner*—Natalie Trousof
*Attorney, Agent, or Firm*—Ladas, Parry, Von Gehr, Goldsmith & Deschamps

[57] ABSTRACT

3,4,5-trimethoxy-phenyl-(1,4-deimethyl-1,2,3,6-tetrahydro-2-pyridyl)-carbinol, and acid addition salts thereof, useful as analgesics, and their preparation are disclosed.

1 Claim, No Drawings

PROCESS FOR THE PREPARATION OF 3,4,5-TRIMETHOXY-PHENYL-(1,4-DIMETHYL-1,2,3,6-TETRAHYDRO-2-PYRIDYL)-CARBINOL

BACKGROUND OF THE INVENTION

This invention relates to 3,4,5-trimethoxyphenyl-(1,4-dimethyl-1,2,3,6-tetrahydro-2-pyridyl)-carbinol having the formula VIII:

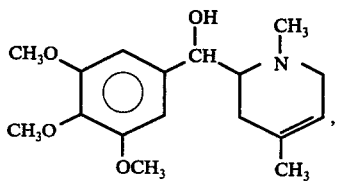

and to acid additional salts thereof.

The formula VIII compound mentioned is a novel substance of use as an analgesic.

SUMMARY OF THE INVENTION AND DESCRIPTION OF THE PREFERRED EMBODIMENTS

The novel product is prepared by the following sequence of reactions:

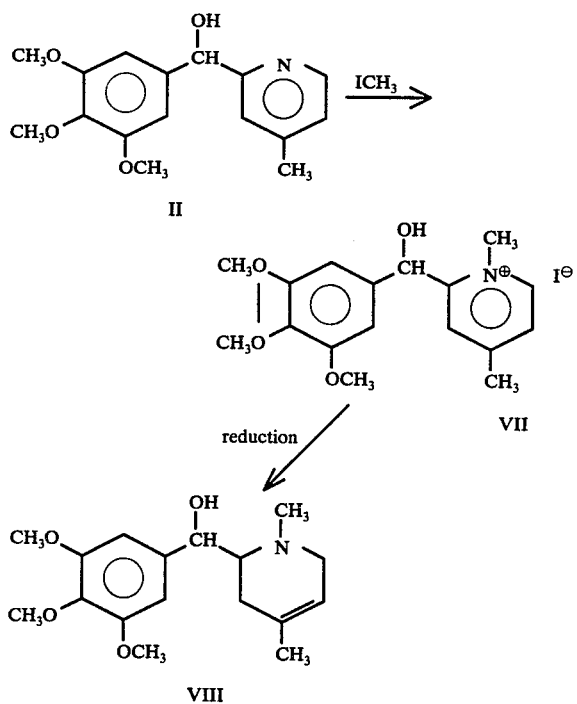

In the first stage of the process the starting compound 3,4,5-trimethoxyphenyl-4(4-methyl-2-pyridyl)-carbinol having the formula II is reacted with methyl iodide, $ICH_3$, to yield product VII which is subjected to a reducing reaction leading to the formula VIII product.

In order to prepare the formula II starting product, 3,4,5-trimethoxybenzaldehyde is made to react under inert atmosphere with 2-bromo-4-methylpyridine in ether solution is the presence of recently prepared butyl-lithium. The reaction is carried out between the temperature of −40° C. maintained in the butyl-lithium addition to the 2-bromo-4-methylpyridine, of −25° C. maintained during the addition of the solution of 3,4,5-trimethoxybenzaldehyde in anhydrous benzene, of −15° C. during the course of the reaction and finally at ambient temperature at the end of the process. The resulting mixture is poured over diluted hydrochloric acid and ice, and the acid layer is neutralized with ammonia flow, precipitating the 3,4,5-trimethoxyphenyl-(4-methyl-2-pyridil) carbinol (II).

The following examples are given purely by way of explanation and in no way limit the scope of the invention.

EXAMPLES

EXAMPLE 1

Preparation of 3,4,5-trimethoxyphenyl-(1,4-dimethyl-2-pyridinyl)-carbinol iodide (VII)

10 ml. of $ICH_3$ are slowly added to a solution of 10 g. of 3,4,5-trimethoxyphenyl-(4-methyl-2-pyridyl) carbinol in 125 ml. of anhydrous acetone and 15 ml. of anhydrous benzene. The resulting mixture is agitated for 1 hour at room temperature, then refluxed for 2 hours, then left to cool, 13.04 g being obtained, with an 87% yield, of a crystalline precipitate identifiable as 3,4,5-trimethoxyphenyl-(1,4-dimethyl-2-pyridinyl)-carbinol iodide. A sample recrystallized from ethanol has a melting point of 162°–163.5° C.

Calculated analysis for $C_{17}H_{22}N\,O_4I$: C, 47.34; H, 5.14; N, 3.25; I, 29.43. Found: C, 47.58; H, 5.26; N, 3.52; I, 29.14.

EXAMPLE 2

Preparation of 3,4,5-trimethoxyphenyl-(1,4-dimethyl-1,2,3,6-tetrahydro-2-pyridyl) carbinol (VIII)

5 g of sodium borohydride are added, with external cooling of the flask, to a solution of 6 g of 3,4,5-trimethoxy-phenyl-(1,4-dimethyl-2-pyridinyl)-carbinol iodide in 50 ml of absolute methanol. The mixture is refluxed for 5 hours, then diluted with water, whereafter the methanol is removed by distillation under reduced pressure and the mixture is extracted with ether. The ether layer when dried yields 2.6 g. of an oil whose hydrochloride recrystallized from ethanol gives a crystalline solid having a melting point of 210°–212° C. and identifiable as 3,4,5-trimethoxyphenyl-(1,4-dimethyl-1,2,3,6-tetrahydro-2-pyridyl)-carbinol.

Analysis calculated for $C_{17}H_{26}O_4NCl$: C, 59.39; H, 7.5; N, 4.08; Cl, 10.33. Found: C, 59.46; H, 7.97; N, 4.27; Cl, 10.52.

PHARMACOLOGICAL PROPERTIES OF THE PRODUCT ACCORDING TO THE INVENTION

Product

VIII — 3,4,5-trimethoxyphenyl-(1,4-dimethyl-1,2,3,6-tetrahydro-2-pyridyl)-carbinol.

The analgesic activity of this compound has been assessed by comparing it with dextropropoxyphene.

A. Acute toxicity

Acute toxicity studies were made in Swiss ICR mice of both sexes weighing 25 ± 2 g. The products were administered intraperitoneally. Acute toxicity calculations were made by the Litchfield-Wilcoxon method.

TABLE 1

| PRODUCT | Lethal Dose 50 ($LD_{50}$) |
| --- | --- |
| VIII | 200.57 mg/kg |
| Dextropropoxyphene | 140 |

B. Analgesic activity

(a) Thermal analgesia

The thermal analgesia effect was studied in Swiss ICR albino mice. The hot-plate technique at 55° C. was used. The rats were divided into batches of 10.

The products being studied were administered intraperitoneally and after 30 minutes the animals were placed on the hot-plate, the time in seconds being counted until the animals started to jump. Batches of control animals which had received injections of distilled water only were used.

The results are given in Table 2.

TABLE 2

| Treatment | Dose | Jumping time in sec $-+$ S.E.M. $\times -$ | Significance of dextro-propoxyphene | Differences from control |
| --- | --- | --- | --- | --- |
| Control | — | 50.1 ± 3.16 | — | — |
| Product VIII | 30 mg/kg | 51.8 ± 5.46 | — | N.S. |
| Dextro-propoxyphene | 30 mg/kg | 91 ± 17.17 | — | p <0.05 |

Product VIII lacks thermal analgesic activity.

(b) Chemical analgesia

The analgesic effect was studied in Swiss ICR albino mice using the acetic acid writhing technique. The animals were divided into batches of 10.

The products studied were administered intraperitoneally and after 30 minutes 0.25 ml of 1% acetic acid was injected intraperitoneally. A batch of control animals was given only the acetic acid. The number of writhings made by each mouse in the 20 minutes after the administration of the acetic acid was counted.

The results are given in Table 3.

TABLE 3

| Treatment | Dose | No. of writhings $-+$ $\times -$ S.E.M. | Significance of dextro-propoxyphene | Differences from control |
| --- | --- | --- | --- | --- |
| Control | — | 93 ± 6.5 | — | — |
| Product VIII | 30 mg./kg. | 58.8 ± 10.2 | N.S. | p < 0.02 |
| Dextro-propoxyphene | 20 mg./kg. | 56.9 ± 9.6 | — | p < 0.01 |

Product VIII has a chemical analgesic activity of the same intensity as dextropropoxyphene.

We claim:

1. A compound selected from the group consisting of 3,4,5-trimethoxyphenyl-(1,4-dimethyl-1,2,3,6-tetrahydro-2-pyridyl)-carbinol and its pharmaceutically acceptable acid addition salts.

* * * * *